United States Patent
Brennan

(10) Patent No.: US 7,670,971 B2
(45) Date of Patent: *Mar. 2, 2010

(54) PRE-MOISTENED NONWOVEN WEBS WITH VISIBLE COMPRESSED SITES

(75) Inventor: Jonathan Paul Brennan, Sharonville, OH (US)

(73) Assignee: The Procter + Gamble Company, Cincinnati, OH (US)

( * ) Notice: Subject to any disclaimer, the term of this patent is extended or adjusted under 35 U.S.C. 154(b) by 185 days.

This patent is subject to a terminal disclaimer.

(21) Appl. No.: 11/303,611

(22) Filed: Dec. 16, 2005

(65) Prior Publication Data

US 2006/0134386 A1 Jun. 22, 2006

Related U.S. Application Data

(60) Provisional application No. 60/638,696, filed on Dec. 22, 2004.

(51) Int. Cl.
*D04H 5/00* (2006.01)
*D04H 5/04* (2006.01)
*B32B 3/00* (2006.01)
*B32B 5/02* (2006.01)
*A61L 15/50* (2006.01)

(52) U.S. Cl. .......................... 442/415; 442/59; 442/97; 442/408; 442/416; 442/417; 428/156; 428/170; 428/171; 428/172; 604/358; 604/367; 604/374; 604/385.01; 604/385.06

(58) Field of Classification Search ................ 442/415, 442/413, 408; 15/208, 209.1
See application file for complete search history.

(56) References Cited

U.S. PATENT DOCUMENTS

| | | | |
|---|---|---|---|
| 3,563,241 A | | 2/1971 | Evans et al. |
| 3,798,120 A | | 3/1974 | Enloe et al. |
| 3,855,046 A | | 12/1974 | Hansen et al. |
| 3,881,210 A | | 5/1975 | Drach et al. |
| 4,612,226 A | * | 9/1986 | Kennette et al. ............ 428/134 |
| 4,755,421 A | | 7/1988 | Manning et al. |
| 5,383,778 A | | 1/1995 | Schulz |
| 5,490,902 A | | 2/1996 | Schulz |
| 5,628,097 A | | 5/1997 | Benson et al. |
| 5,629,081 A | | 5/1997 | Richards et al. |

(Continued)

FOREIGN PATENT DOCUMENTS

CA 841938 A * 5/1970

(Continued)

OTHER PUBLICATIONS

U.S. Appl. No. 11/166,925, filed Jun. 23, 2005, Sheehan et al.

(Continued)

*Primary Examiner*—Jennifer A Chriss
(74) *Attorney, Agent, or Firm*—C. Brant Cook; Jay A. Krebs; Julie A. McConihay

(57) ABSTRACT

The disclosure relates to pre-moistened webs and wipes having visible compressed sites that provide the perception of a cloth-like texture. The disclosure also relates to a nonwoven web made of non-thermoplastic fibers with at least one compressed site on the surface of the web that remains visible when the web is pre-moistened.

6 Claims, 5 Drawing Sheets

U.S. PATENT DOCUMENTS

| | | | |
|---|---|---|---|
| 5,658,639 A | 8/1997 | Curro et al. | |
| 5,725,821 A * | 3/1998 | Gannon et al. | 264/203 |
| 6,013,349 A * | 1/2000 | Takeuchi et al. | 428/152 |
| 6,093,665 A | 7/2000 | Sayovitz et al. | |
| 6,127,593 A | 10/2000 | Bjorkquist et al. | |
| 6,190,502 B1 | 2/2001 | Takeuchi et al. | |
| 6,361,784 B1 | 3/2002 | Brennan et al. | |
| 6,432,272 B1 | 8/2002 | Hollenberg et al. | |
| 6,433,245 B1 | 8/2002 | Bjorkquist et al. | |
| 6,544,912 B1 | 4/2003 | Tanio et al. | |
| 6,613,954 B1 | 9/2003 | Horney et al. | |
| 6,670,521 B2 | 12/2003 | Noda et al. | |
| 6,675,702 B1 * | 1/2004 | Maksimow | 100/41 |
| 6,749,718 B2 * | 6/2004 | Takai et al. | 162/115 |
| 2001/0023160 A1 * | 9/2001 | Yamada et al. | 442/413 |
| 2002/0022427 A1 | 2/2002 | Curro et al. | |
| 2002/0168911 A1 * | 11/2002 | Tonner | 442/405 |
| 2002/0177827 A1 | 11/2002 | Noda et al. | |
| 2004/0198114 A1 | 10/2004 | Barnholtz et al. | |

FOREIGN PATENT DOCUMENTS

| | | |
|---|---|---|
| WO | WO 02/066089 A2 | 8/2002 |
| WO | WO 2006/004871 A1 | 1/2006 |

OTHER PUBLICATIONS

PCT International Search Report dated Jun. 28, 2006, 3 pages.

* cited by examiner

PRE-MOISTENED NONWOVEN WEBS WITH VISIBLE COMPRESSED SITES

CROSS REFERENCE TO RELATED APPLICATIONS

This application claims the benefit of U.S. Provisional Application No. 60/638,696, filed Dec. 22, 2004.

FIELD OF INVENTION

The present invention relates to disposable pre-moistened nonwoven webs and wipes comprised thereof.

BACKGROUND OF INVENTION

Consumers of disposable pre-moistened nonwoven wipes, particularly baby wipes, desire a soft, cloth-like wipe that is economical. Consumers react to visual and tactile properties in their assessment of wipes. Thus the presence of cloth-like texture on a pre-moistened nonwoven wipe can signal to a consumer that a wipe has the properties of cloth.

Disposable pre-moistened wipes are typically made of non-woven webs. A variety of methods are known in the art for providing non-woven webs with cloth-like texture. However, in order for the texture to be visible when a web is pre-moistened, the methods may require physical or chemical binding of the fibers that make up the web. For example, visible texture may be applied to a non-woven web comprising thermoplastic fibers via thermal calender-bonding. In this process, adjacent thermoplastic fibers are compressed and melt-bonded together. In a further example, an adhesive may be applied to the fibers. For instance, the Procter & Gamble Company of Cincinnati, Ohio. markets PAMPERS® Kid Fresh™ wipes in North America, which comprise nonwoven substrates manufactured via an airlaid adhesive-bonded process that includes the imprinting of calender embossed designs. In another example, a resin may hold embossed regions together when wet, such as in the 100% cellulosic Bounty® Paper Towels, also marketed by the Procter & Gamble Company.

The use of additives, such as chemicals, binders, resins and the like, may add to the cost of producing pre-moistened nonwoven wipes. Likewise, the increasing price of petroleum-based products such as thermoplastic fibers, may add to the cost. To provide the consumer with a soft, cloth-like wipe that is economical, it would therefore be desirable to provide a pre-moistened nonwoven wipe consisting essentially of non-thermoplastic fibers with a visible cloth-like texture that withstands being wetted without using chemicals, binders, resins and the like to maintain the texture. Moreover, it would be desirable to provide a method for doing so.

SUMMARY OF INVENTION

The present invention relates to pre-moistened webs and wipes consisting essentially of non-thermoplastic fibers and having visible compressed sites comprising un-melted fibers that may provide the perception of a cloth-like texture. The present inventors have surprisingly discovered that the compressed sites remain visible when wet even though the webs and wipes of the present invention do not contain thermoplastic fibers which may melt-bond in the compressed sites. The present inventors have also surprisingly found that the compressed sites remain visible without the need of a material amount of a binder which would chemically bond the fibers in the compressed sites. Thus the wet visibility of the compressed sites of the present invention is accomplished without using methods known in the art which are based upon binding fibers together, such as via the application of chemicals or excess binder, or by melt-bonding thermoplastic fibers.

In one embodiment, the invention relates to a nonwoven web consisting essentially of non-thermoplastic fibers wherein at least about 20% of the non-thermoplastic fibers have a fiber length of at least about 18 millimeters (mm). The nonwoven web has at least one compressed site located on its surface. The compressed site comprises un-melted fibers and is visible when the web is pre-moistened.

In another embodiment, the invention relates to a method of making a pre-moistened nonwoven web that has at least one compressed site that is visible. The method comprises the following steps. In one step, at least one nonwoven web comprising a surface is provided. The nonwoven web comprises non-thermoplastic fibers, wherein at least about 20% of the non-thermoplastic fibers have a fiber length of at least about 18 mm. In a further step, a compressive stress of at least about 200 Newtons per square meter ($N/m^2$) is applied to the web to create at least one compressed site on a surface of the web. In a further step, the wipe is pre-moistened.

In yet another embodiment, the invention relates to a pre-moistened wipe comprising a carded spunlaced web. The carded spunlaced web is in turn comprised of: (a) from about 20% to about 80% rayon fibers and from about 80% to about 20% pulp fibers, wherein the rayon fibers have a fiber length of at least about 18 mm; (b) a surface; and (c) a plurality of compressed sites comprising un-melted fibers. The compressed sites are located on the surface and are visible when the web is pre-moistened.

BRIEF DESCRIPTION OF DRAWINGS

The features, aspects and advantages of the present invention will become better understood with reference to the following description, appended claims and accompanying drawings where:

DETAILED DESCRIPTION OF INVENTION

Definitions

Figure 1:
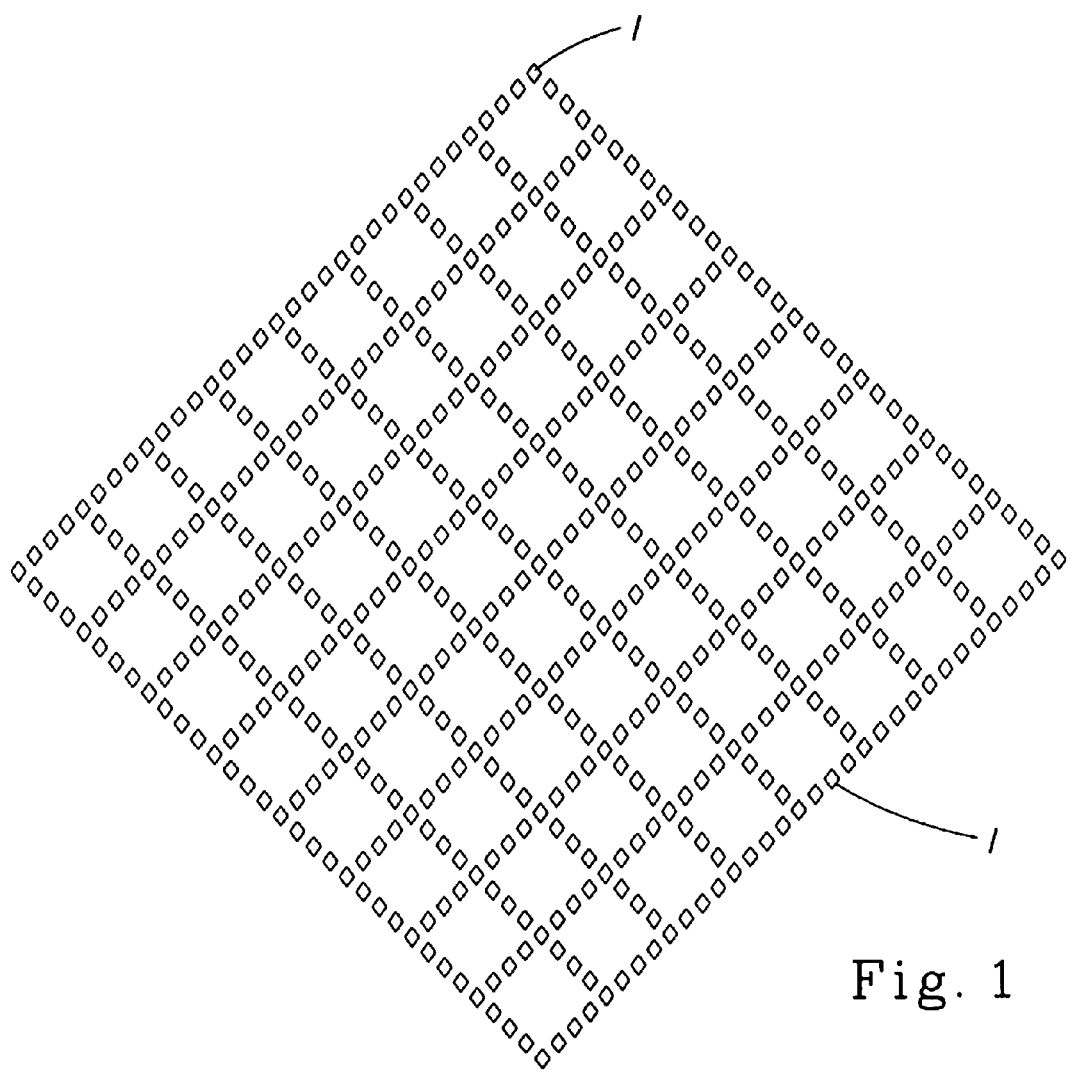
FIG. 1 is a view of one pattern of the compressed sites of the present invention.

"Fiber" as used herein, refers to the unit which forms the basic element of the web disclosed herein.

"Nonwoven web" or "web" are used interchangeably herein, and refer to a layer or layers of fibers that are laid and bonded via nonwoven manufacturing processes known in the art. "Wipe" as used herein refers to an article that is comprised of one or more layers of web.

"Non-thermoplastic fiber" as used herein, refers to a fiber that does not act as a thermoplastic fiber which softens or melts upon exposure to heat and returns to its original state when cooled to room temperature.

"Surface" as used herein, refers to a two-dimensional external or superficial layer of a web or wipe.

"Compressive stress" as used herein, refers to the blunt force which, when applied to a web, produces a "compressed site". Compressive stress may not include shear force, which when applied to a web, cuts the fibers comprising the web. Compressive stress is measured in units of Newtons per square millimeter (N/mm$^2$).

"Compressed site" as used herein, refers to an area of the web in which the fibers comprising the web are pressed together such that fibers are brought closer together in space as compared to the fibers that are located in the uncompressed regions. A compressed site may have a higher fiber density as compared to the uncompressed regions.

"Un-melted fibers" as used herein, refers to the fibers in the compressed sites, which are compressed by a blunt force to form a functional solid material in which there is no softening or melting of the fibers and consequently no bonding between the fibers, i.e. no mixing between the fibers on the molecular level. Therefore, if one could seize and pull on a single fiber in a compressed site, it would separate from other fibers in the compressed site.

"Uncompressed regions" as used herein, refers to those areas of the web that do not contain a compressed site. The fibers comprising the uncompressed regions of the web may remain in a substantially unaltered form after the web is subjected to compressive stress.

"Visible" as used herein, refers to being capable of being seen by the naked eye when viewed at a distance of 12 inches (in), or 30.48 centimeters (cm), under the unimpeded light of an ordinary incandescent 60 watt light bulb that is inserted in a fixture such as a table lamp.

"Liquid composition" as used herein, refers to any liquid, including, but not limited to a pure liquid such as water, a colloid, an emulsion, a suspension, a solution, a lotion and mixtures thereof. The term "aqueous solution" as used herein, refers to a solution that is at least about 20%, at least about 40%, or even at least about 50% water by weight, and at most about 95% water by weight, about 90% water by weight, or even at most about 80% water by weight.

"Pre-moistened" as used herein may refer to a web or wipe which is wetted, or is comprised of a portion that is wetted, with a liquid composition prior to use by the consumer. "Pre-moistened" may also refer to webs or wipes that are wetted with a liquid composition prior to packaging, such as in a generally moisture impervious container or wrapper. Such pre-moistened wipes, which may also be referred to as "wet wipes" and "towelettes", may be suitable for use in cleaning tasks related babies, children and adults. Such wipes may also be suitable for use in the application of substances to the body, including but not limited to make-up, skin conditioners, ointments, medications and combinations thereof. Such wipes may also be of use for the cleaning or grooming of pets, or for the general cleansing of surfaces and objects, such as household kitchen and bathroom surfaces, eyeglasses, exercise and athletic equipment, automotive surfaces and the like.

"Prints" as used herein refers to any ink or polymer that is added to the surface of a web or wipe to provide aesthetic appeal. Prints may take any form including, but not limited to, indicia, figures, patterns, letters, pictures, words, phrases and combinations thereof.

"Binder" as used herein, refers to any compound added to a nonwoven web that may improve the strength of the web by binding its constituent fibers together, i.e., via chemical bonding. Some binders may disassociate from the web when subjected to the conditions encountered by the web during or after disposal. Such conditions may include, but are not limited to, large amounts of water, particular pHs, water with particular ion concentrations and combinations thereof. When the web comprising the binder is exposed to particular conditions, the binder may dissolve, for example. When the binder dissolves, the strength of the web may decrease and in turn the dispersibility of the web may increase. Binders, for example, may be water soluble, water-swellable and combinations thereof. Polyvinyl alcohol (PVOH) and EP919, which is a flushable, dispersible binder sold by Air Products of Allentown, Pa., USA, are non-limiting examples of binders. Further examples of binders may include, but are not limited to, sulfonic-acid modified PVOH, carboxylic-acid modified PVOH, and binders comprising at least one compound selected from the group consisting of a water-soluble organic salt, a water-soluble inorganic salt and a boron compound. A further non-limiting example of a binder may include water-insoluble or water-swellable carboxymethylcellulose. The solubility of carboxymethylcellulose may depend on its degree of etherification and pH, among other factors.

"Water soluble" as used herein, refers to a component that is soluble or otherwise dispersible (such as to provide a micellar solution) in water at a level of at least about 0.25 percent by weight at about 25 degrees Centigrade.

When used herein in relation to material compositions, the terms "%", "percent", "weight percent" or "percent by weight" refer to the quantity by weight of a component as a percentage of the total weight, unless otherwise indicated.

As used herein with respect to webs, the term "machine-direction" or "MD" refers to the direction of web travel as the web is produced, for example on commercial nonwoven production equipment. Likewise, the term "cross-direction" or "CD" refers to the direction perpendicular to the machine direction and parallel to the general plane of the layered fibrous product and/or layered fibrous structure. With respect to individual wipes, the terms refer to the corresponding directions of the wipe with respect to the web used to produce the wipe. These directions are carefully distinguished herein, because the mechanical properties of a nonwoven web may differ depending on how the nonwoven web is oriented during testing. For example, tensile properties of a web may differ between the machine-direction and the cross-direction, due to the orientation of the constituent fibers, and other process-related factors.

"Comprising" or "comprised of" as used herein, refers to the various components, ingredients or steps that may be conjointly employed in practicing the present invention. Accordingly, the terms "comprising" or "comprised of" may encompass the more restrictive terms "consisting essentially of" and "consisting of".

"Surfactant" as used herein, refers to materials which may preferably orient toward an interface. Classes of surfactants may include, but are not limited to: nonionic surfactants, anionic surfactants, cationic surfactants, amphoteric surfactants, zwitterionic surfactants and mixtures thereof.

"Emulsifier" and "solubilizer" may be interchangeably used herein, and refer to components that may reduce the tendency of one or more other components in a lotion composition to phase separate from the lotion.

"Co-surfactant" as used herein, refers to a component that may act as either a surfactant or an emulsifier/solubilizer.

"Organic water soluble polymer" as used herein, refers to an organic compound formed by the joining of smaller molecules, referred to as monomers. The term may be used to refer either to a macromolecule made up of a large number of monomers linked by covalent bonds, e.g., polypeptides, nucleic acids, polysaccharides, and plastics, or to a protein made up of several subunits linked by covalent or no covalent bonds, e.g., hemoglobin or IBM immunoglobulin.

Nonwoven Web

The nonwoven webs of the present invention may be made via fiber laying and fiber bonding processes known in the art. Fiber laying processes of use include, but are not limited to, spunlaying, meltblowing, carding, airlaying, wetlaying and combinations thereof. Fiber bonding steps of use include, but are not limited to, spunlacing (i.e. hydroentanglement), cold calendering, hot calendering, air thru bonding, chemical bonding, needle punching and combinations thereof. One preferred process for producing the soft, flexible, cloth-like webs of the present invention is by carding and spunlacing the fibers.

The nonwoven webs of the present invention consist essentially of non-thermoplastic fibers. As used herein, the phrase "consists essentially of non-thermoplastic fibers" means that no more than about 10% by weight of the fibers may be thermoplastic. In a further embodiment, no more than about 8% by weight of the fibers may be thermoplastic. In yet another embodiment, no more than about 5% by weight of the fibers may be thermoplastic.

It is believed that the presence of more than about 10% by weight of thermoplastic fibers in a nonwoven web affects the formation of the compressed sites. Without wishing to be bound by theory, it is believed that once the amount of thermoplastic fibers in a nonwoven web is increased to above about 10%, there are sufficient numbers of thermoplastic fibers randomly distributed throughout the web such that when the compressed sites are made, the associated softening and/or melting of the thermoplastic fibers (particularly if heat is conjointly applied with the compressive stress) may cause melt-bonding between adjacent thermoplastic fibers. The melt-bonding of thermoplastic fibers is commonly known in the art as a method for providing nonwoven webs with visible texture that withstands moistening. Therefore, a thermoplastic fiber content of above about 10% by weight would bring a nonwoven web outside of the scope of the present invention.

The nonwoven webs of the present invention may comprise less than about 10% of thermoplastic fibers. This low amount of thermoplastic fibers may provide benefits that are unrelated to the formation of the compressed sites and their enduring visibility when moistened. Such benefits may include, but are not limited to, dust control, softness, and combinations thereof.

Fiber length is measured prior to the fiber laying and bonding processes. In the present invention at least about 20% of the non-thermoplastic fibers have a fiber length of at least about 18 mm; this requirement may ensure good in-use strength in the pre-moistened webs. The fibers of use in the present invention may have a fiber length of: at least about 18 mm; at least about 20 mm; at least about 25 mm; at least about 30 mm; at least about 35 mm; or even at least about 38 mm. The fibers of use in the present invention may be essentially continuous and may have a length that is theoretically infinite. It is also advantageous to use these relatively long fibers as they provide the nonwoven web with a soft, cloth-like hand.

The fibers may have an average fiber decitex (dtex) of at least about 0.8 dtex, at least about 1 dtex, at least about 1.2 dtex, or even at least about 1.5 dtex. The fibers may have an average decitex of less than about 8 dtex, less than about 5 dtex, or even less than about 2 dtex.

The nonwoven webs of the present invention may comprise thermoplastic fibers, non-thermoplastic fibers and mixtures thereof. Non-limiting examples of non-thermoplastic fibers that may be of use include: rayon, which in turn includes but is not limited to viscose, lyocell and mixtures thereof; pulp; cotton; wool; silk; jute; linen; ramie; hemp; flax; camel hair; kenaf; and mixtures thereof. Non-limiting examples of thermoplastic fibers that may be of use include: polypropylene and copolymers of polypropylene; polyethylene and copolymers of polyethylene; polyamides and copolymers of polyamides; polyesters and copolymers of polyesters; aliphatic polyesteramides; lactic acid polymers; and lactide polymers; polyhydroxyalkanoates; and mixtures thereof.

In one embodiment of the present invention, the nonwoven webs may comprise from about 20% to about 80% rayon fibers and from about 80% to about 20% of pulp fibers. In another embodiment, the nonwoven webs may comprise from about 30% to about 70% rayon fibers and from about 70% to about 30% pulp fibers. In another embodiment, the nonwoven webs may comprise from about 40% to about 60% rayon fibers and from about 60% to about 40% pulp fibers. In yet another embodiment, the nonwoven webs may comprise about 60% rayon fibers and about 40% pulp fibers.

The nonwoven webs of the present invention may further comprise less than about 10% of a binder. Such a low amount of binder may provide benefits that are unrelated to the formation of the compressed sites and the visibility of the sites when moistened. Binder may be added as what is known in the art as a "dusting layer". A dusting layer is a small amount of binder that is added to fibers during the fiber laying process so that the fibers will slightly adhere and not fly off the forming surface. In some embodiments of the present invention, the nonwoven webs may comprise less than about 10%, less than about 5%, or even less than about 2% binder. In further embodiments, the nonwoven webs may comprise less than about 1%, or even less than about 0.5% binder. In some embodiments of the present invention, the nonwoven webs may comprise 0% binder.

The nonwoven webs of the present invention may have basis weights ranging from about 5 to about 200 grams per square meter (gsm), from about 10 to about 175 gsm, from about 30 to about 150 gsm, from about 20 to about 100 gsm, from about 30 to about 70 gsm, or even from about 40 to about 60 gsm.

The resulting nonwoven webs may be soft, cloth-like, flexible, biodegradable and combinations thereof. Providing the nonwoven webs with the compressed sites of the present invention may result in nonwoven webs which retain good in-use strength, yet that have cloth-like texture that is visible when the webs are pre-moistened. The texture is provided through the application of the compressed sites of the present invention.

Compressed Sites

The nonwoven webs of the present invention comprise at least one compressed site. To impart compressed sites to the nonwoven web, any method of applying compressive stress to the web may be used. Methods of applying compressive stress to the web include, but are not limited to, stamping, pressing, cold calender rolling, heated calender rolling and combinations thereof. The compressive stress may smash or compress the fibers with a blunt force, in contrast to other methods of applying stress in which the fibers are sheared or cut with a sharp edge. Without wishing to be bound by theory, it is believed that the blunt force has less impact on the in-use strength of the web since it mainly weakens the fibers at the edge of the compressed site, instead of cutting them.

The discrete compressed site(s) may take any shape and may be randomly situated on the web or may form a pattern. Examples of compressed sites (1) and patterns thereof include, but are not limited to, those shown in FIGS. 1 and 2, as well as variations thereof.

Figure 2:
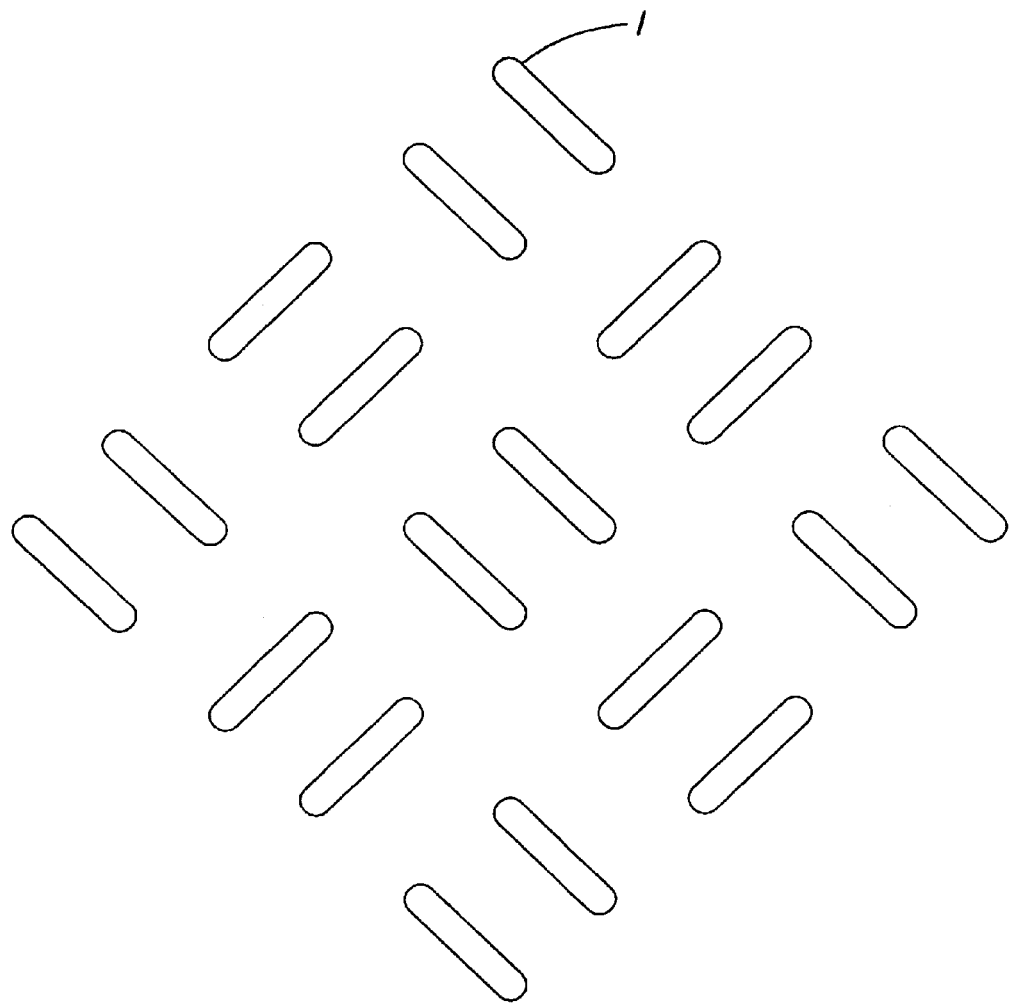
FIG. 2 is a view of another pattern of the compressed sites of the present invention.
Figure 3:
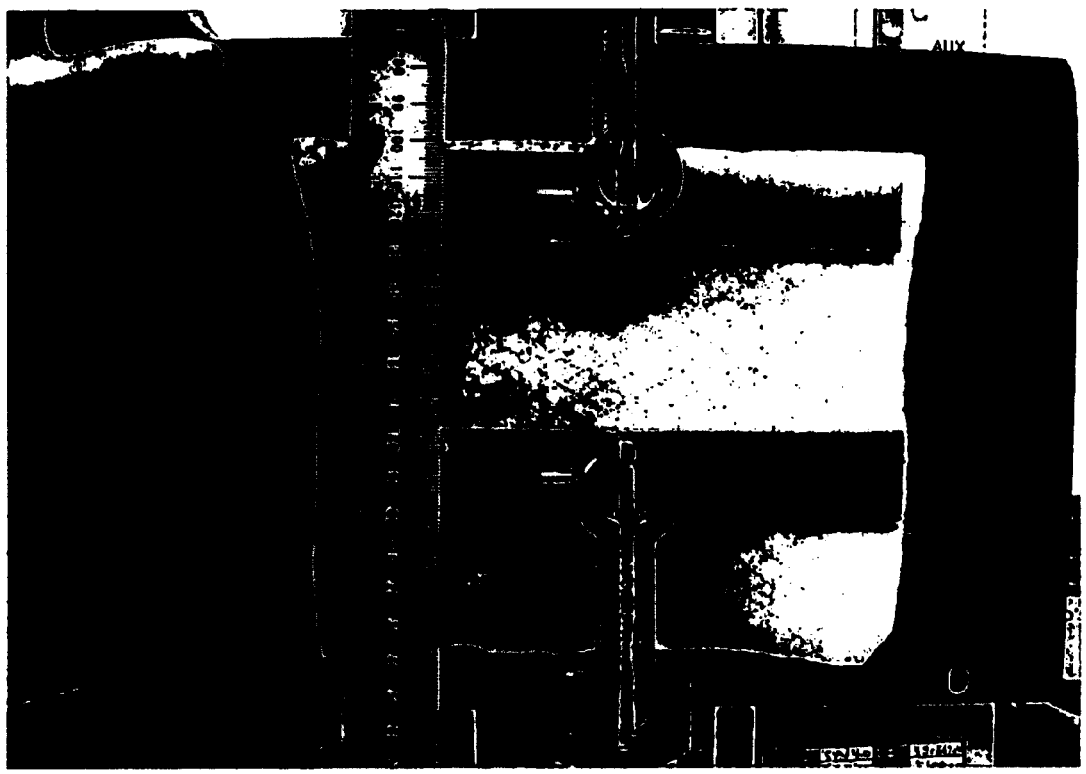
FIG. 3 is a view of a pre-moistened web with the pattern of compressed sites of FIG. 1.
Figure 4:
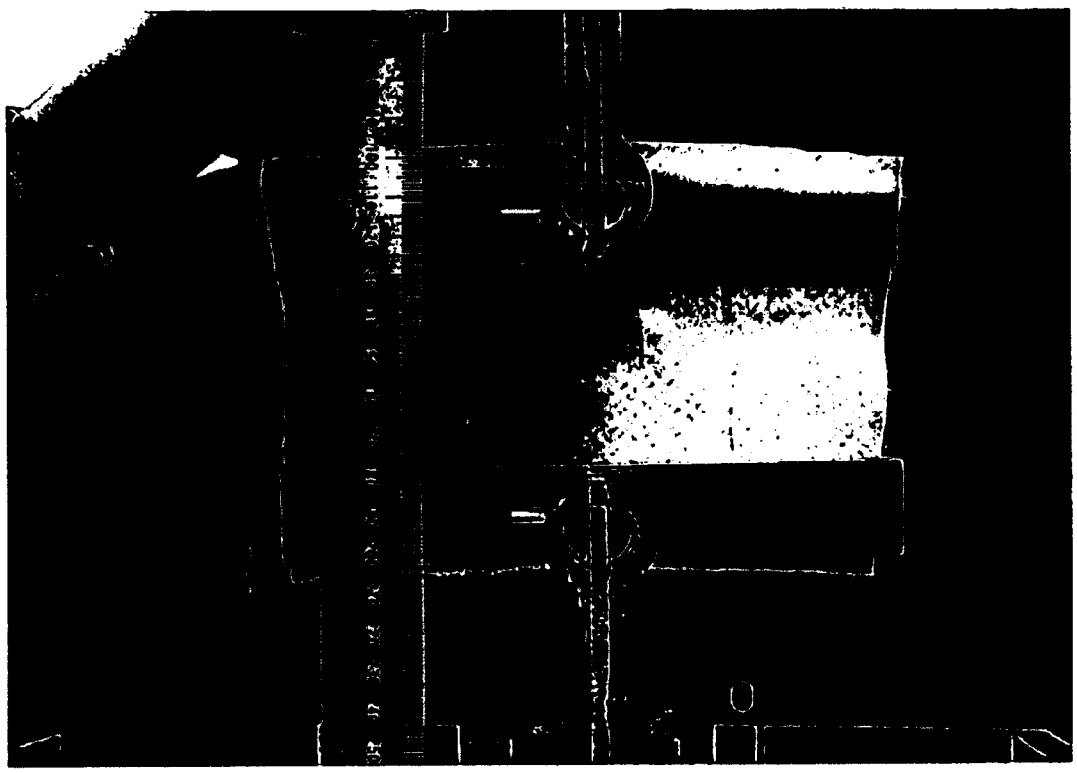
FIG. 4 is a view of a pre-moistened web with the pattern of compressed sites of FIG. 2.

In one embodiment of the present invention, a pre-moistened, carded spunlaced web comprising 100% rayon is provided with a pattern of compressed sites via cold calender rolling and is shown in FIG. 3. The carded spunlaced web is compressed between a smooth calender roller and a patterned calender roller at ambient temperature. The patterned calender roller has a nip pattern similar to that shown in FIG. 1. The total raised surface area of the nips equals about 12.6% of the total surface area of the patterned roller. The calendered web acquires compressed sites where it contacts the nips of the patterned roller. FIG. 4 shows another embodiment of a pre-moistened, carded spunlaced web comprising 100% rayon that has been provided with compressed sites using a similar process, but with a patterned calender roller that has a nip pattern similar to that shown in FIG. 2.

Figure 5:
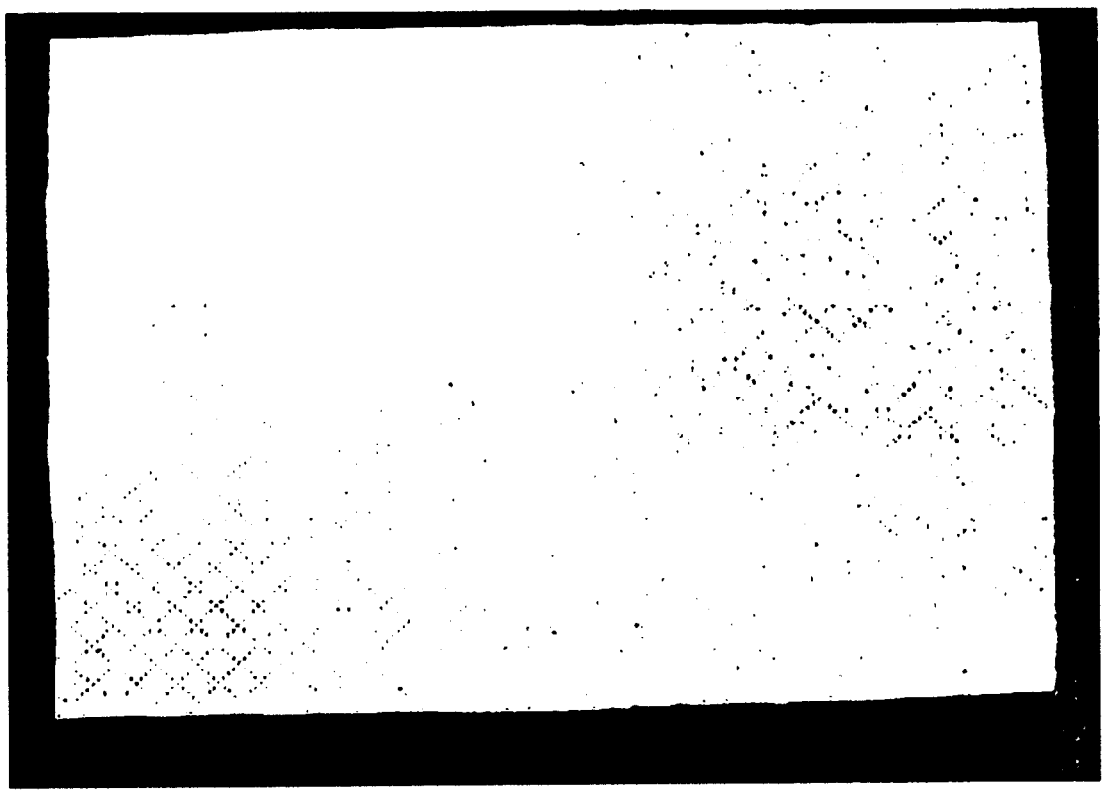
FIG. 5 is a view of a pre-moistened web with the pattern of compressed sites of FIG. 1.

In yet a further embodiment, a pre-moistened, carded spunlaced web comprising 60% lyocell and 40% pulp is provided with a pattern of compressed sites via heated calender rolling and is shown in FIG. 5. The carded spunlaced web is compressed between a smooth calender roller and a patterned calender roller both of which have internal temperatures of about 350° F. The patterned calender roller has a nip pattern similar to that shown in FIG. 1. The total raised surface area of the nips equals about 12.6% of the total surface area of the patterned roller. The calendered web acquires compressed sites where it contacts the nips of the patterned roller.

The compressive stress applied to the substrate is calculated by dividing the total force by the compression area of the patterned roller, as shown in the sample calculation in Table 1, and is based on the assumption that the entire load is transferred though the raised area of the patterned roller. After compression, a silicone based liquid composition is applied to pre-moisten the web, at a ratio of about 3 grams of liquid composition to about 1 gram of dry substrate. As shown in FIG. 3, the compressed sites provide the web with a cloth-like texture that is visible when wet.

TABLE 1

Calendering Compressive Stress Sample Calculation

|  | English |  | Metric |  |
| --- | --- | --- | --- | --- |
| Cylinder Diameter | 4 | [in] | 101.6 | [mm] |
| Total Cylinder Area | 12.6 | [in$^2$] | 8107.3 | [mm$^2$] |
| Cylinder Pressure | 300 | Pounds per square inch [psi] | 2.0684 | [N/mm$^2$] |
| Cylinder Force | 3770 | [lb] | 16769.5 | [N] |
| Number of Cylinders | 2 |  | 2 |  |
| Total Force | 7540 | [lb] | 33539.0 | [N] |
| Roll Face Width | 16 | [in] | 406.4 | [mm] |
| PLI Loading | 471 | [pli] | 82.5 | [N/mm] |
| Total Raised Surface Area | 12.6% | [%] | 12.6% | [%] |
| Compression Width | 0.063 | [in] | 1.5875 | [mm] |
| Compression Area | 0.126 | [in$^2$] | 81.3 | [mm$^2$] |
| Compressive Stress | 59840 | [psi] | 413 | [N/mm$^2$] |

As a result of the compressive stress, the fiber density in the compressed sites may be higher as compared to the density of the uncompressed regions of the web. Without wishing to be bound by theory, it is believed that when the compressive stress applied to the web is at least about 200 N/mm$^2$, the compressed sites remain denser than the uncompressed regions even when the web is pre-moistened. Consequently, the cloth-like texture provided by the compressed sites is visible when the web is wet. In further embodiments of the present invention, the compressive stress may range from about 250 to about 500 N/mm, or from about 275 to about 450 N/mm$^2$.

As long as the compressive stress is at least about 200 N/mm$^2$, it may be applied to the web using any number of different nip patterns (See FIG. 4 for example, which shows a pre-moistened 100% non-thermoplastic carded spunlaced web with compressed sites in a nip pattern similar to that shown in FIG. 2). However, in the present invention, the maximum total raised surface area of the nip or nips may be less than about 25%, less than about 20%, less than about 19%, less than about 17% or even less than about 13% of the surface area of the patterned roller. The minimum total raised surface area of the nip or nips may be greater than about 3%.

The maximum total raised surface area of the nip or nips may be limited in the present invention on the following basis. Without wishing to be bound by theory, it is believed that the cylinder force that would be required to apply a compressive stress of at least about 200 N/mm$^2$ through a total raised surface area that is greater than about 20% is outside of the realm of conventional calendar capability. As shown in Table 1, the patterned roller already withstands a force as high as 3,770 pounds or 16769.5 Newtons to apply a compressive stress of 413 N/mm$^2$ through a raised nip surface area of 12.6%.

Wipes

Wipes may be comprised of one or more layers of the web of the present invention. The wipes may be adapted for a variety of uses and may be pre-moistened or moistened with a liquid composition. The liquid composition may comprise an aqueous solution and may further comprise surfactant, co-surfactant, foam building agent, emulsifier, non-cellulosic water soluble organic polymer and mixtures thereof.

The wipes of the present invention may be suitable for use in cleaning babies, and may also find use in cleaning tasks related to persons of all ages. Such wipes may also include articles used for application of substances to the body, including but not limited to application of make-up, skin conditioners, ointments, medications and mixtures thereof. Such wipes may also include articles used for the cleaning or grooming of pets, and articles used for the general cleansing of surfaces and objects, such as household kitchen and bathroom surfaces, eyeglasses, exercise and athletic equipment, automotive surfaces and the like. Such wipes may also be used in the hospital or clinical environment to clean up bodily fluids and the like.

In some embodiments of the present invention, the wipes may be strong enough so that their integrity is retained when they are subjected to typical in-use forces, which may range from about 2 Newtons (N) to about 10 N. The strength of the wipes may be determined by measuring their tensile strength; this may be accomplished by cutting samples of wipes into 50 mm wide strips and testing them for tensile strength using EDANA method 20.2-89 in both the cross direction and machine direction. Using this method, the stretching force necessary to cause the integrity of a wipe or a portion of a wipe to fail is measured and is referred to as the wipe's "maximum force." Maximum force is measured in Newtons.

Embodiments of the wipes of the present invention may have an MD maximum force from about 8 to about 100 N, from about 16 to about 80 N, or even from about 32 to about 64 N. Embodiments of the wipes of the present invention may have a CD maximum force from about 2 to about 25 N, from about 4 to about 20 N, or even from about 8 to about 16 N. In further examples, the wipes may have an MD or CD force with a numerical value anywhere between these specifically disclosed upper and lower values.

In one embodiment of the present invention the wipes may be "pop-up" wipes, such that when one wipe is pulled from a container such as a tub, an edge of the next wipe in the stack may be presented for easy dispensing. The wipes may be folded and stacked in a container such as a tub. The wipes of the present invention may be folded in any of various known folding patterns, such as C-folding and Z-folding. Use of a Z-fold pattern may enable a folded stack of wipes to be interleaved with overlapping portions. Fold patterns are disclosed more fully in commonly assigned, co-pending U.S. patent application Ser. No. 09/344695.

The wipes of the present invention may further comprise prints, which may provide aesthetic appeal.

All documents cited in the Detailed Description of the Invention are, in relevant part, incorporated herein by reference; the citation of any document is not to be construed as an admission that it is prior art with respect to the present invention. To the extent that any meaning or definition of a term in this written document conflicts with any meaning or definition of the term in a document incorporated by reference, the meaning or definition assigned to the term in this written document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A premoistened nonwoven web, said web consisting essentially of at least 90% by weight of non-thermoplastic fibers comprising rayon fibers and pulp fiber, wherein at least 20% by weight of said non-thermoplastic fibers have a fiber length of at least 18 mm and wherein said web comprises a greater amount of rayon fibers than pulp fibers, wherein said web comprises:
    (a) a surface;
    (b) a plurality of visible compressed sites formed under a compressive stress of at least 200 N/mm$^2$ located on said surface, said compressed sites comprising un-melted, weakened fibers providing a cloth-like texture that is maintained even when wet; and
    (c) a binder.

2. The nonwoven web of claim 1, wherein said web is carded and spunlaced.

3. The nonwoven web of claim 1, wherein said rayon fibers are selected from the group consisting of: viscose, lyocell and mixtures thereof.

4. The nonwoven web of claim 1, wherein said web comprises less than or equal to 10% by weight of binder.

5. A wipe comprising the nonwoven web of claim 1, wherein said wipe has a basis weight of from about 30 to about 150 grams per square meter and is pre-moistened with a lotion.

6. The wipe of claim 5, wherein said wipe is further comprised of prints.

* * * * *